s011052182B2

United States Patent
Spickermann et al.

(10) Patent No.: US 11,052,182 B2
(45) Date of Patent: Jul. 6, 2021

(54) METHOD AND APPARATUS FOR CHECKING A DIALYZER FOR THE PRESENCE OF A LEAK

(71) Applicant: FRESENIUS MEDICAL CARE DEUTSCHLAND GMBH, Bad Homburg (DE)

(72) Inventors: Reiner Spickermann, Wasserlosen-Burghausen (DE); Gerhard Wiesen, Bad Homburg (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 0 days.

(21) Appl. No.: 16/064,197

(22) PCT Filed: Dec. 23, 2016

(86) PCT No.: PCT/EP2016/002182
§ 371 (c)(1),
(2) Date: Jun. 20, 2018

(87) PCT Pub. No.: WO2017/108196
PCT Pub. Date: Jun. 29, 2017

(65) Prior Publication Data
US 2019/0001043 A1 Jan. 3, 2019

(30) Foreign Application Priority Data
Dec. 23, 2015 (DE) ..................... 10 2015 016 842.8

(51) Int. Cl.
*A61M 1/16* (2006.01)
*B01D 61/28* (2006.01)
(Continued)

(52) U.S. Cl.
CPC ............ *A61M 1/1684* (2014.02); *A61M 1/16* (2013.01); *A61M 1/3652* (2014.02); *B01D 61/28* (2013.01);
(Continued)

(58) Field of Classification Search
None
See application file for complete search history.

(56) References Cited

U.S. PATENT DOCUMENTS 5,185,082 A * 2/1993 Nakano ................... A61L 2/022
210/639
5,863,421 A 1/1999 Peter, Jr. et al.
(Continued)

FOREIGN PATENT DOCUMENTS

DE 3442744 6/1986
DE 3923078 9/1990
(Continued)

*Primary Examiner* — Richard C Gurtowski
(74) *Attorney, Agent, or Firm* — Jacobson Holman PLLC

(57) ABSTRACT

The present invention relates to a method for checking a dialyzer for the presence of a leak in the semipermeable membrane of the dialyzer, wherein the membrane divides the inner dialyzer space into a least one blood chamber and into at least one dialyzate chamber, wherein the blood chamber is flowed through by blood in the operation of the dialyzer and is in fluid communication with a blood-side line system and the vascular system of the patient, and wherein the dialyzate chamber is flowed through by dialysis fluid in the operation of the dialyzer and is in fluid communication with a dialyzate-side line system, wherein the method comprises the following steps:

a) emptying the blood chamber or the dialyzate chamber of blood and of dialysis fluid respectively and keeping the fluid (blood or dialyzate) in the non-emptied dialyzate chamber or blood chamber;
(Continued)

b) building up a test pressure by means of a gas, in particular by means of air, in the emptied blood chamber or in the emptied dialyzate chamber; and c) measuring the pressure drop over time in the emptied blood chamber or in the emptied dialyzate chamber or in the line system respectively in fluid communication therewith and/or measuring the pressure increase in the non-emptied blood chamber or in the non-emptied dialyzate chamber or in the line system respectively in fluid communication therewith or measuring the number of air bubbles or of a parameter correlated with the number of air bubbles in the non-emptied blood chamber or in the non-emptied dialyzate chamber or in a line system respectively in fluid communication therewith, wherein the steps a) to c) are carried out subsequent to the blood treatment of the patient and subsequent to the disconnection of the patient from the blood-side line system.

15 Claims, 3 Drawing Sheets

(51) Int. Cl.
    *B01D 65/10*     (2006.01)
    *A61M 1/36*     (2006.01)

(52) U.S. Cl.
    CPC ....... *B01D 65/104* (2013.01); *A61M 2205/15* (2013.01); *A61M 2205/3331* (2013.01); *A61M 2205/705* (2013.01)

(56) References Cited

U.S. PATENT DOCUMENTS

| | | |
|---|---|---|
| 6,804,991 B2 | 10/2004 | Balschat et al. |
| 8,241,237 B2 | 8/2012 | Gatti et al. |
| 2005/0126998 A1* | 6/2005 | Childers ................. A61M 1/28 |
| | | 210/646 |

FOREIGN PATENT DOCUMENTS

| | | |
|---|---|---|
| DE | 69837395 | 11/2007 |
| DE | 102008005516 | 2/2009 |
| JP | 2003190747 | 7/2003 |
| WO | WO 2013/017236 | 2/2013 |

* cited by examiner

METHOD AND APPARATUS FOR CHECKING A DIALYZER FOR THE PRESENCE OF A LEAK

BACKGROUND OF THE INVENTION

1. Field of the Invention

The present invention relates to a method for checking a dialyzer for the presence of a leak in the semipermeable dialyzer membrane which separates the inner space of the dialyzer into at least one blood chamber and into at least one dialyzate chamber, wherein the blood chamber is in fluid communication with a blood-side line system which is connected to the vascular system of a patient during the treatment, and wherein the dialyzate chamber is in fluid communication with a dialyzate-side line system such that the blood flows through the blood-side line system and the blood chamber and the dialyzing fluid flows through the dialyzate chamber and the dialyzate-side line system during the blood treatment.

2. Description of Related Art

Microleaks in the membrane of the dialyzer which have a leak rate of less than 0.5 ml/min can in particular not be recognized using previously known methods. A leak in the membrane of a dialyzer through which blood moves out of the blood chamber into the dialyzate chamber of the dialyzer and thus into the dialyzate-side line system of a dialysis device is admittedly unproblematic during an ongoing treatment, but requires the disinfection of the dialysis device before a subsequent dialysis treatment to prevent a cross-contamination or a contamination of the subsequently treated patient.

A method is known from U.S. Pat. No. 6,804,991 B2 in which a leak can be recognized in the fluid system of a blood treatment unit. The method is based on the measurement of a pressure change during the treatment of the patient.

WO 2013/017236 A1 relates to a method of checking the function of medical functional devices such as extracorporeal blood hoses. The method comprises the pressure build-up and the measurement of the pressure change over time. The method of WO 2013/017236 A1 is carried out before starting the treatment of a patient.

U.S. Pat. No. 8,241,237 B2 relates to a method of pressure measurement in a blood-conducting line. A sensor which is protected from direct contact with the patient's blood by a special filter arrangement serves the pressure measurement. If a malfunction of the sensor is determined after the blood treatment, the sensor or its defective parts are replaced.

SUMMARY OF THE INVENTION

It is the underlying object of the present invention to provide a method and an apparatus by means of which a leak, and in particular a microleak, of the membrane of a dialyzer can be determined particularly precisely.

This object is achieved by a method having the features described herein and by an apparatus having the features described herein.

The method in accordance with the invention comprises the following steps:
a) emptying the blood chamber or the dialyzate chamber of blood and of dialysis fluid respectively and keeping the fluid (blood or dialyzate) in the non-emptied dialyzate chamber or blood chamber;
b) building up a test pressure in the emptied blood chamber or in the emptied dialyzate chamber; and
c) measuring the pressure drop over time in the emptied blood chamber or dialyzate chamber or in the line system respectively in fluid communication therewith or measuring the pressure increase in the non-emptied blood chamber or dialyzate chamber or in the line system respectively in fluid communication therewith or measuring the number of air bubbles or a parameter correlated with the number of air bubbles in the non-emptied blood chamber or in the non-emptied dialyzate chamber or in the line systems respectively in fluid communication therewith,
wherein the steps a) to c) are carried out subsequent to the blood treatment of the patient and subsequent to the disconnection of the patient from the blood-side line system.

Provision is thus made in accordance with the invention to empty the blood chamber or dialyzate chamber or the total line system respectively in fluid communication therewith, i.e. the blood-side line system or the dialyzate-side line system, to build up a pressure in the chamber or line system emptied in this manner and then to measure the pressure development over time.

The term "emptied" within the framework of the present invention relates to the fact that the fluid was emptied, i.e. the blood was completely or partially removed from the blood chamber or from the blood-side line system or dialysis fluid was removed from the dialyzate chamber or out of the dialyzate-side line system.

It is furthermore pointed out that the term "a" does not necessarily refer to exactly one of the elements in question, but rather also covers a plurality of these elements.

A compartment of the dialyzer (blood side or dialyzate side) is thus first emptied, then a test pressure is built up on the side filled by air or by another gas (the intact wet membrane wall is non-permeable for air) and the pressure development over time is subsequently observed. Due to the solubility of gas in air, there is always a slight pressure drop on that side at which the test pressure was applied; however, with a membrane leak the pressure drop is considerably larger and/or a movement of air bubbles takes place into the non-emptied side. These bubbles can then be led past the bubble detector and based on this or based on the pressure development, a conclusion on a leak of the membrane can be made.

The movement of the bubbles over the defective membrane of the dialyzer results in a drop of the air pressure in the air-filled or gas-filled, pressurized compartment or in the line system communicating therewith and results in a pressure increase on the liquid-filled side.

Microleaks having a diameter in the μm range and larger can also be determined in the dialyzer membrane with this procedure. An intact dialyzer membrane has pores in the nm range so that a substantial difference results in the pressure behavior between an intact membrane and a defective membrane. Microleaks having a diameter below the μm range can thus also be determined. They can, for example, be diameters of several tenths of a μm.

The test only works for a limited time period because the pressure gradient degrades. However, the difference in the pressure development between a defective membrane and an intact membrane is very large so that an observation time of <20 s is preferably sufficient.

Provision is made in a preferred embodiment of the invention that no disinfection of the dialyzate-side line system is carried out subsequent to the check if no leak was found in the membrane of the dialyzer on the check. It is thus a substantial advantage of the invention that in this case the previously required disinfection of the dialyzate-side fluid system can be dispensed with.

The measurement of the pressure can generally be carried out in the dialyzate chamber, in the dialyzate line system, in the blood chamber or in the blood-side line system or in a plurality of the aforesaid positions.

The dialyzate chamber and/or the line system in fluid communication therewith is also called a "dialyzate side" in the following, and the blood chamber and/or the line system in fluid communication therewith is/are also called a "blood side" in the following.

Provision is made in an embodiment of the invention that at least one bubble detector is arranged in the blood-side line system and/or in the dialyzate-side line system and is configured to measure air bubbles in the blood or in the dialysis fluid; and that the check for a leak of the membrane is carried out on the basis of the number of air bubbles or on the basis of a parameter correlated therewith. If a test pressure is applied to the fluid-emptied side by air or by another gas and if the dialyzer membrane has a leak, a movement of the air or of the gas into the non-emptied blood side or dialyzate side takes place and thus air bubbles are produced on this side of the system.

To be able to detect them, a bubble detector can be used which detects the number of air bubbles led past said bubble detector per unit of time. The blood pump or the dialyzate pump can be set into operation for this purpose to achieve a movement of the blood or of the dialysis fluid and thus also of the air bubbles located therein.

It is conceivable that the build-up of the test pressure is carried out a multiple of times and a continuation is only made with step c) when the drop of the test pressure over time does not exceed a limit value. In this procedure, the blood side or the dialyzate side is emptied first and then a test pressure is applied to the emptied blood side or dialyzate side and the pressure development is measured. The non-emptied side (blood side or dialyzate side) is not closed during this time, but is rather e.g. connected to a drain. If the pressure drop per unit of time exceeds a limit value, a test pressure is again built up and the pressure drop over time is measured. Only when the latter remains below a limit value is the method continued with step c).

The build-up of the test pressure preferably takes place by means of a compressor which conveys environmental air into the blood side or dialyzate side which has been or is to be emptied.

Provision can be made in accordance with the invention that the pressure development or the number of detected bubbles or the parameter correlated therewith is displayed and/or that an evaluation is made on the basis of one or more of these measured values as to whether the membrane has a leak and the result of the evaluation is displayed. In the latter case, it can immediately be signaled to a user by a display whether the last used dialyzer was intact and whether thus a disinfection of the dialyzate side can be dispensed with.

The present invention furthermore relates to an apparatus for checking a dialyzer for the presence of a membrane leak comprising the dialyzer which is separated by at least one semipermeable membrane into at least one blood chamber and into at least one dialyzate chamber, comprising at least one blood-side line system which is in fluid communication with the blood chamber and which is connected to the blood chamber and to the vascular system of a patient during the treatment and comprising at least one dialyzate-side line system in fluid communication with the dialyzate chamber, wherein the blood flows through the blood-side line system and the blood chamber and the dialysis fluid flows through the dialyzate chamber and the dialysis fluid system during the blood treatment, i.e. during the operation of the dialysis device, wherein the apparatus has at least one control unit as well as means controlled by this unit which are configured to carry out the method steps described herein.

These means are preferably one or more valves, pumps and/or compressors.

It is conceivable that the apparatus has one or more pressure sensors which are arranged at the dialyzate chamber, at the dialyzate-side line system, at the blood chamber or at the blood-side line system or in a plurality of the aforesaid elements and that the apparatus is preferably configured to detect the pressure development over time and to make a conclusion on the presence of a leak of the dialyzer based thereon.

For this purpose, the apparatus can have a display unit and/or an evaluation unit which displays the pressure development over time and/or which evaluates it as to whether it is in an acceptable range or not. The same applies accordingly to the presence or to the number of detected air bubbles.

The apparatus preferably has at least one bubble detector in the blood-side line system and/or in the dialyzate-side line system, said bubble detector being configured to measure air bubbles in the fluid (blood or dialysis fluid). The apparatus can furthermore have means which are configured such that they carry out the check of the leak-tightness of the membrane of the dialyzer on the basis of the number of air bubbles or of a parameter correlated therewith.

The apparatus can have means, in particular one or more pumps and/or compressors, for the emptying of the blood from the blood chamber and/or for the emptying of the dialysis fluid from the dialyzate chamber. Means, in particular at least one compressor, can furthermore be provided for the introduction of pressurized air into the blood chamber emptied of blood or into the blood side or into the dialyzate chamber emptied of dialysis fluid or into the dialyzate side.

The present invention furthermore relates to a dialysis device, preferably a device for carrying out a hemodialysis, a hemofiltration or a hemodiafiltration, wherein the device has at least one apparatus as described herein.

BRIEF DESCRIPTION OF THE DRAWINGS

Further details and advantages of the invention will be explained in more detail with reference to an embodiment shown in the drawings. There are shown.

DETAILED DESCRIPTION OF THE PREFERRED EMBODIMENTS

Figure 1:
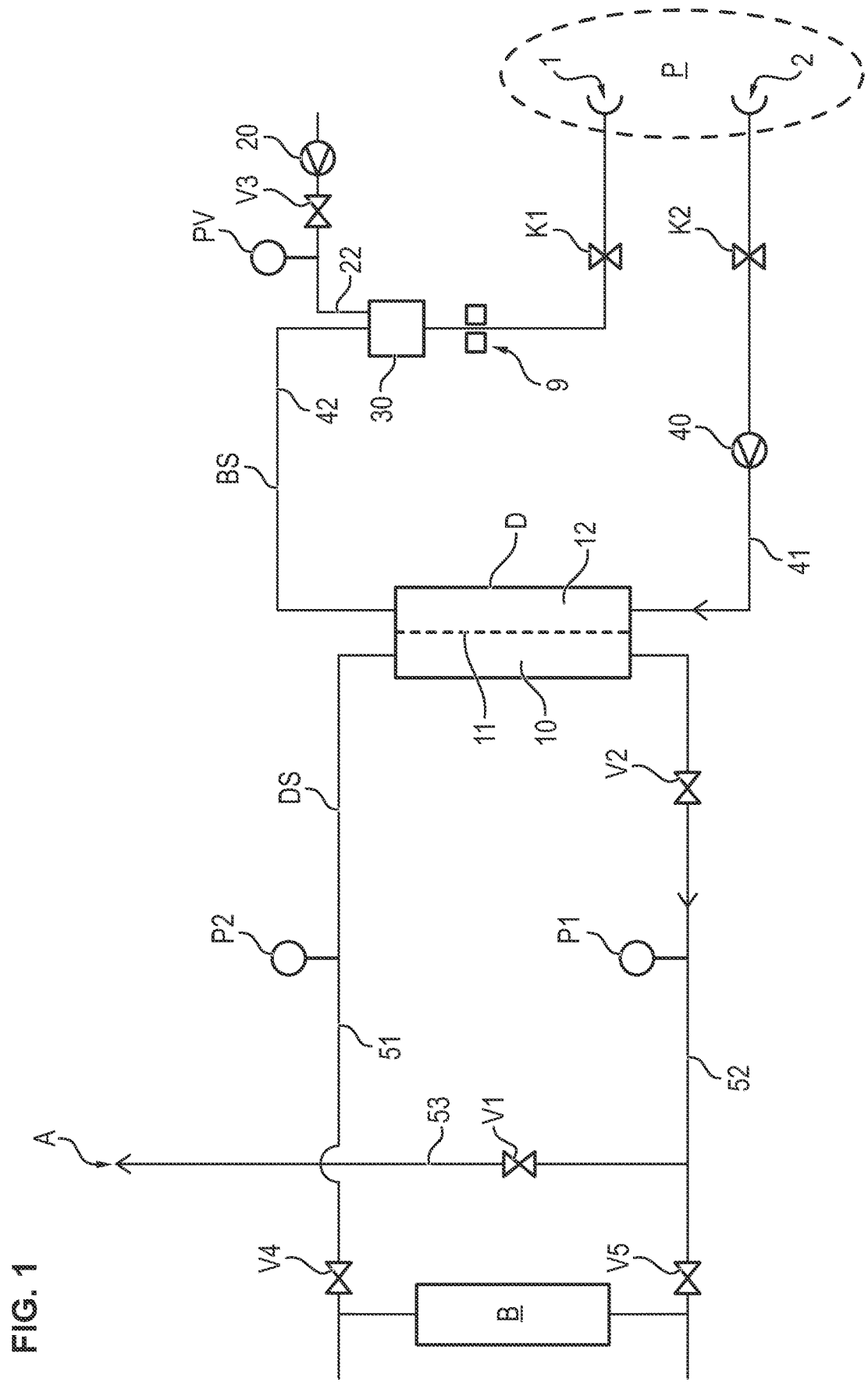
FIG. 1: a schematic view of the dialyzate side and of the blood side of a dialysis device.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

Reference symbol D indicates the dialyzer which is divided by a semipermeable membrane 11, which is preferably formed by a bundle of hollow fibers, into a dialyzate chamber 10 and into a blood chamber 12.

The blood-side line system BS, which forms the extracorporeal blood circuit, is in communication with the blood chamber 12. The blood pump 40 is located upstream of the dialyzer D and the clamp K2 is located upstream of the blood pump 40 in the blood-side line system BS. The venous drip chamber 30 is located downstream of the dialyzer D. The venous clamp K1 is arranged downstream thereof.

The terms "upstream" and "downstream" relate to the direction of flow of the blood with a blood pump 40 in operation, said direction of flow being marked by an arrow in the Figure.

Not only the hose line which represents a component of the blood-side line system BS opens into the drip chamber 30, but also a further line 22. The compressor which conveys air out of the environment into the blood-side line system BS for carrying out the method is located in this further line 22. The valve V3 is located between the compressor 20 and the drip chamber 30. The reference symbol PV indicates a pressure sensor which is located in the venous part of the blood-side line system.

Reference numerals 1 and 2 indicate the arterial and venous connectors of the extracorporeal circuit and the latter is or can be connected by them to the vascular system of the patient P.

In the operation of the blood pump 40, blood is conveyed, with a connected patient, through the line 41 to the dialyzer D and from the dialyzer D through the line 42 and the drip chamber 30 back to the patient.

The dialyzate-side line system DS is located on the dialyzate side and has lines, in particular hose lines, by means of which dialysis fluid is guided into or out of the dialyzate chamber 10 in the operation of the device. The movement of the dialysis fluid in the dialyzate-side line system DS is carried out by a pump, not shown.

The terms "upstream" and "downstream" relate to the direction of flow of the dialysis fluid with a pump for the dialysis fluid in operation, said direction of flow being marked by an arrow in the Figure. Fresh dialysis fluid is conveyed to the dialyzer D through the line 51. Consumed dialysis fluid is extracted from the dialyzer D through the line 52.

A respective pressure sensor P1 and P2 is located upstream and downstream of the dialyzer in the dialyzate-side line system DS, as can be seen from FIG. 1.

Reference symbol B schematically indicate the balancing system which serves the balancing of the dialysis fluid supplied to and removed from the dialyzer D and which communicates with the supplying and removing lines 51 and 52. The lines 51 and 52 or the balancing system can be blocked by valves V4, V5.

The line 53 branches off from the line 52 leading away from the dialyzer D and leads to the outflow A for consumed dialysis fluid.

As can be seen from FIG. 1, the valve V2, by means of which the line 52 can be closed, is located between the dialyzer D and the branching of the line 53 in the line 52. A further valve V1 is arranged in the line 53. The line 53 can be blocked by means of the valve V1.

Instead of the above-named clamps K1, K2, valves or also any other desired blocking means can also be used. The position of the clamps is also exemplary, i.e. the clamps can also be arranged at another place or in a different number.

Instead of the above-named valves V1, V2, V3, V4, V5, clamps or also any other desired blocking means can also be used. The position of the valves is also exemplary, i.e. the clamps can also be arranged at another place or in a different number.

Two test sequences are described by way of example in the following by means of which it can be determined whether the membrane 11 has one or more leaks or is intact.

In a first embodiment, the blood side is first emptied of blood.

The clamps K1 and K2 are closed. The blood pump 40 is switched off. The balancing chamber system B is blocked by closing the valves V4, V5. This applies to the total test procedure in this embodiment.

The compressor 20 is switched on, the valve V3 is opened and the valves V1 and V2 are opened.

The blood located on the blood side is displaced by the air over the membrane 11 to the dialyzate side. It moves from there, with open valves V1, V2, through the lines 52 and 53 into the drain A.

The compressor remains in operation for so long until a pressure increase is determined by means of the pressure sensor PV.

The compressor 20 is then switched off and the valve V1 is closed.

The build-up of the test pressure on the blood side emptied from blood starts subsequent to this. The blood pump 40 remains switched off for this purpose and the balancing chamber system B is blocked. The compressor 20 is switched on while the valve V1 is closed and the valve V2 remains open. The compressor 20 remains switched on for so long until a specific pressure, e.g. 1250 mm Hg, is reached at the pressure sensor PV at the blood side.

The compressor is then switched off, the valve V3 is closed and the valve V1 is opened. A check is then made whether the pressure drop per time on the blood side now vented or filled with pressurized air exceeds a limit value. If this is the case, the procedure is repeated, i.e. the compressor 20 is switched on and the valve V3 is opened again. The valve V1 is closed and the valve V2 is opened. The compressor is then switched off, the valve V3 is closed and the valve V1 is opened. The pressure development over time is subsequently determined at the pressure sensor PV.

This process is repeated until the pressure drop per time on the blood side does not exceed a limit value.

If this is the case, the actual pressure holding test begins. For this purpose, the compressor 20 is switched off, the valve V3 is closed and the valve V1 is closed. The balancing chamber system B remains blocked. The pressure holding test is thus carried out when the dialyzate side filled with dialysis fluid is closed, i.e. when the supply and removal lines of the dialyzate side are blocked. This allows an air intake into the dialyzate side to be measured precisely by a pressure increase on the dialyzate side.

After switching off the compressor 20 and after the closing of the valve V1, the pressure development on the dialyzate side is determined by means of the pressure sensor(s) P1 and/or P2. The filter D is qualified as in order if the pressure increase over time measured by the sensor(s) P1 and P2 does not exceed a limit value, i.e. if the pressure increase measured at the dialyzate side is comparatively small.

If this is not the case, however, i.e. if the pressure at the sensors P1 and/or P2 increases comparatively fast, this is due to a leak of the filter membrane 11. A conclusion can thus be drawn from the speed of the pressure increase measured at the dialyzate side on whether the membrane of the dialyzer D is in order or has one or more leaks.

If the pressure increase measured by means of the sensors P1 and P2 is not identical, this indicates an air intake into the hydraulics so that a hydrostatic pressure difference due to air intake results in this deviation.

Alternatively or additionally to the measurement of the pressure increase on the dialyzate side, the measurement of the pressure drop on the blood side is also conceivable during the pressure holding test.

Figure 2:
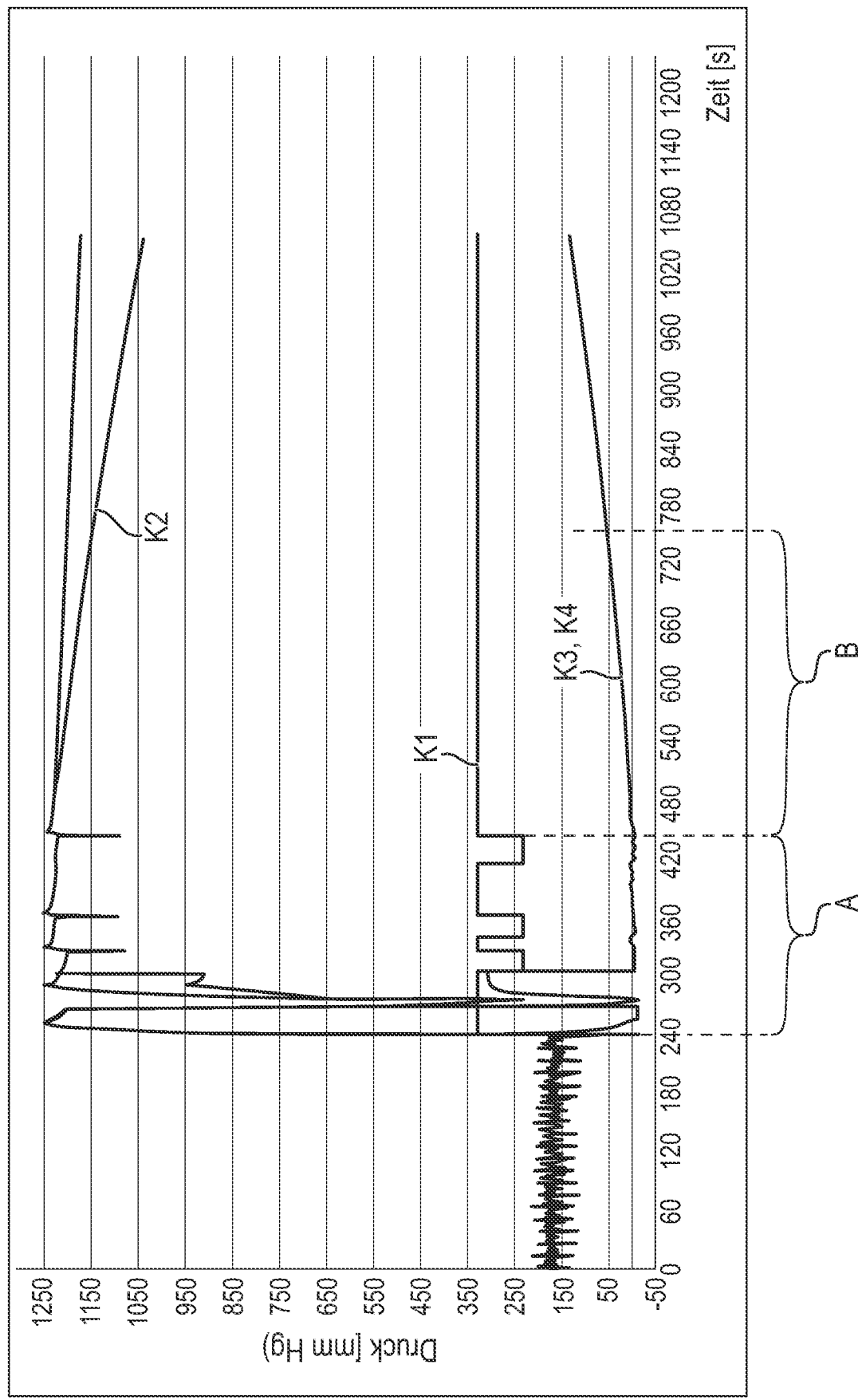
FIG. 2: pressure developments over time for an intact dialyzer membrane.
Figure 3:
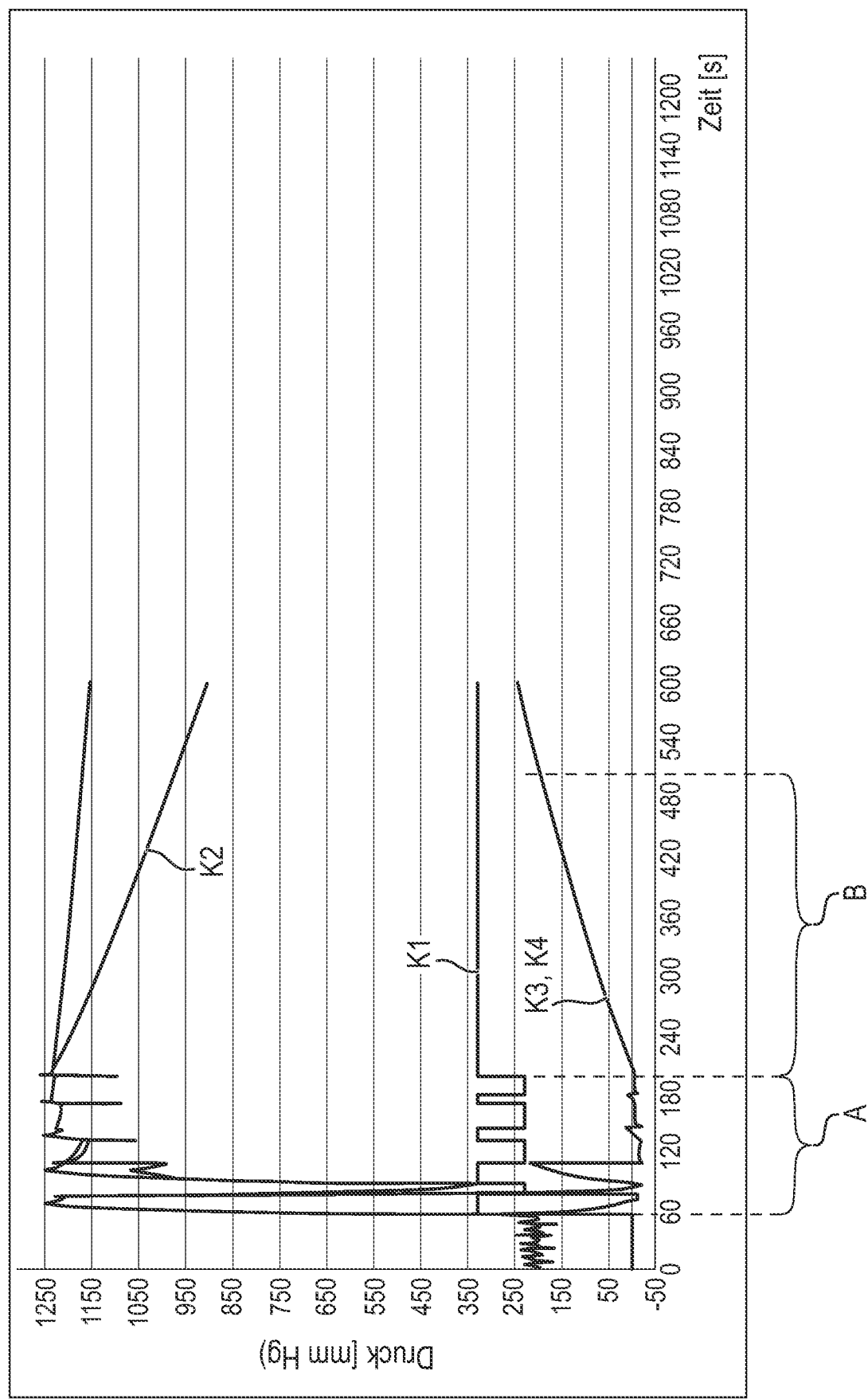
FIG. 3: pressure developments over time for a defective dialyzer membrane.

FIG. 2 shows the result of the pressure development over time for an intact membrane and FIG. 3 for a defective filter in which the membrane has one or more leaks.

The above-described build-up of the test pressure on the blood side by a repeated opening and closing of the valve V1 takes place in the time period A and is indicated by the curve K1. The respective higher value shows the closed valve V1, the respective lower value shows the opened valve V1.

The curve K2 shows the pressure development measured at the pressure sensor PV. As can be seen from FIG. 2, the pressure build-up with air on the emptied blood side is repeated so often until the pressure loss with opened valves V1 and V2 does not exceed a specific limit value per time unit.

The pressure holding test only starts with the beginning of section B when this requirement is satisfied. This is carried out while the dialyzate side is closed with respect to the drain A and overall so dialysis fluid can neither be supplied nor removed.

The curves K3 and K4 show the pressure developments over time measured at the sensors P1 and P2. It results from FIG. 2 that the pressure increase in the range of approximately 50 mm Hg in approximately 5 min. from the start of section B. This is an acceptable value in the embodiment described here so that a conclusion can be drawn from this of an intact, i.e. leak-free membrane.

In contrast, with the measurement result in accordance with FIG. 3, the pressure increase measured at the sensors P1 and P2 is in a range of approximately 200 mm Hg in approximately 5 min. from the start of section B, which is above a limit value. A conclusion of a defective membrane is made in this case.

The named values are naturally only examples which do not restrict the invention.

The second embodiment starts with the disconnection of the patient by closing the clamps K1 and K2 and by stopping the blood pump 40. The compressor 20 is switched off and the valve V3 is closed so that the blood side is closed overall.

The emptying of the dialyzate side by means of a standard emptying program then follows through the line 52 with opened valves V1 and V2 to the drain A. A venting valve or the compressor can be provided in the line 51 for the emptying. The dialyzate coupling is open on the running of the emptying program.

The valve V2 is subsequently closed and a test pressure is built up by means of air or of another gas on the dialyzate side emptied of dialysis fluid. This pressure build-up takes place by means of a compressor until the desired test pressure, e.g. 1250 mm Hg, is reached. The compressor is stopped.

As soon as this is the case, the valve V2 is closed and the connectors 1 and 2 are connected to one another so that a closed blood circuit is formed. The blood pump 40 is taken into operation.

The air bubble detector 9, which is arranged downstream of the drip chamber 30, for example, detects the number of air bubbles per time unit with a running blood pump 40. The membrane 11 is qualified as intact when the counted number of air bubbles per time unit does not reach a limit value; otherwise a conclusion is drawn on a defective membrane.

Alternatively or, additionally, the pressure is measured at the dialyzate-side pressure sensors P1 and P2. It is conceivable that the result of this pressure measurement and also the measured value of the air bubble detector is used for determining the integrity of the membrane 11.

It is thus possible, for example, that a conclusion is only made on an intact membrane when the number of air bubbles per time unit remains beneath a limit value and, in addition, the pressure loss on the dialyzate side does not exceed a limit value.

Microleaks in a dialyzer can be recognized by means of the present invention. The process takes place after the disconnection of the patient and after the carrying out of the blood treatment. Cross-contaminations can also be avoided by the process without any subsequent disinfection of the dialyzate side.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

What is claimed is:

1. A method of checking a dialyzer (D) for the presence of a leak in a semipermeable membrane of the dialyzer (D), the membrane dividing an inner dialyzer space into at least one blood chamber and into at least one dialyzate chamber, the blood chamber being flowed through by blood during operation of the dialyzer and being in fluid communication with a blood-side line system (BS) and a vascular system of a patient (P), and the dialyzate chamber being flowed through by a dialysis fluid during operation of the dialyzer and being in fluid communication with a dialyzate-side line system (DS), said method comprising the following steps:
   a) emptying the blood chamber or the dialyzate chamber of blood and of dialysis fluid, respectively, and keeping the fluid (blood or dialyzate) in the non-emptied dialyzate chamber or blood chamber;
   b) building up a test pressure via a gas in the emptied blood chamber or in e emptied dialyzate chamber and measuring the test pressure; and
   c) measuring a pressure increase in the non-emptied blood chamber or in the non-emptied dialyzate chamber or in the line system (BS, DS), respectively, in fluid communication therewith,
   the steps a) to c) being carried out subsequent to a blood treatment of the patient (P) and subsequent to disconnection of the patient (P) from the blood-side line system (BS), and
   the step b) build-up of the test pressure and the measuring of the test pressure being carried out multiple times, and a continuation only being made with step c) when a drop of the measured test pressure over time does not exceed a limit value.

2. The method in accordance with claim 1, wherein, subsequent to the carrying out of steps a) to c), no disinfection of the dialysate-side line system (DS) is carried out if no leak was detected in the membrane of the dialyzer (D).

3. The method in accordance with claim 1, wherein the step of measuring the pressure is carried out in the dialysate chamber, in the dialyzate-side line system (DS), in the blood chamber, or in the blood-side line system (BS), or in a plurality thereof.

4. The method in accordance with claim 1, wherein the step c) is carried out while the non-emptied chamber or the non-emptied line system (BS, DS) is closed.

5. The method in accordance with claim 1, wherein the build-up of the test pressure in step b) is carried out via a compressor which conveys environmental air into the emptied blood chamber or dialyzate chamber or in the line system (LS, DS) in communication therewith.

6. The method in accordance with claim 1, wherein pressure development is displayed and/or an evaluation is made based on one or more of measured values as to whether the membrane has a leak, and the result of the evaluation is displayed.

7. An apparatus for checking a dialyzer (D) for the presence of a leak in a semipermeable membrane of the dialyzer (D), said apparatus comprising:
the dialyzer (D), which is divided by the semipermeable membrane into at least one blood chamber and into at least one dialyzate chamber, including at least one blood-side line system (BS) which is in fluid communication with the blood chamber and with a vascular system of a patient (P) during a treatment, and including at least one dialyzate-side line system (DS) in fluid communication with the dialyzate chamber, blood flowing through the blood-side line system (BS) and the blood chamber, and dialysis fluid flowing through the dialyzate chamber and the dialysis fluid system (DS) during the treatment; and
a control unit, and elements which are controlled by the control unit, and are configured to carry out the method steps in accordance with claim 1.

8. The apparatus in accordance with claim 7, wherein the apparatus has one or more pressure sensors which are arranged indirectly or directly at the dialyzate chamber, at the dialyzate-side line system (DS), at the blood chamber, or at the blood-side line system (BS), or in a plurality thereof, and wherein the apparatus is configured to detect pressure development over time.

9. The apparatus in accordance with claim 7, further comprising a device for emptying the blood from the blood chamber and/or for emptying the dialysis fluid from the dialyzate chamber and a device for introducing pressurized air into the blood chamber emptied of blood or into the dialyzate chamber emptied of dialysis fluid.

10. The apparatus in accordance with claim 7, further comprising a display device configured to display pressure development and/or an evaluation unit configured to carry out an evaluation based on one or more of measured values to determine whether the membrane has a leak, and to display a result of the evaluation.

11. A dialysis device comprising at least one apparatus in accordance with claim 7.

12. The method according to claim 1, wherein the gas is air.

13. The apparatus according to claim 8, wherein, based on the pressure development over time, the apparatus determines whether a leak in the semipermeable membrane is present.

14. The apparatus according to claim 9, wherein the device for introducing pressurized air is a compressor.

15. The apparatus according to claim 9, wherein the pressurized air is introduced into the line system (LS, DS).

* * * * *